United States Patent [19]
Douglas

[11] Patent Number: 6,097,984
[45] Date of Patent: Aug. 1, 2000

[54] SYSTEM AND METHOD OF STIMULATION FOR TREATING GASTRO-ESOPHAGEAL REFLUX DISEASE

[75] Inventor: Donald Douglas, Lewisburg, Pa.

[73] Assignee: Medtronic, Inc., Minneapolis, Minn.

[21] Appl. No.: 09/199,152

[22] Filed: Nov. 25, 1998

[51] Int. Cl.[7] ........................................... A61N 1/18
[52] U.S. Cl. ................................ 607/40; 607/133
[58] Field of Search .................... 607/2, 40, 41, 607/133; 128/898

[56] References Cited

U.S. PATENT DOCUMENTS

| | | | |
|---|---|---|---|
| 4,168,703 | 9/1979 | Kenigsberg | 128/748 |
| 4,561,963 | 12/1985 | Owen et al. | 204/43 |
| 4,774,956 | 10/1988 | Kruse et al. | 128/635 |
| 4,887,610 | 12/1989 | Mittal | 128/733 |
| 5,117,827 | 6/1992 | Stuebe et al. | 128/635 |
| 5,178,145 | 1/1993 | Rea | 128/642 |
| 5,188,104 | 2/1993 | Wernicke et al. | 607/40 |
| 5,292,344 | 3/1994 | Douglas | 607/40 |
| 5,314,473 | 5/1994 | Godin | 623/12 |
| 5,423,872 | 6/1995 | Cigaina | 607/40 |
| 5,479,935 | 1/1996 | Essen-Moller | 128/734 |
| 5,540,730 | 7/1996 | Terry, Jr. et al. | 607/40 |
| 5,582,699 | 12/1996 | Melzer | 204/420 |
| 5,690,691 | 11/1997 | Chen et al. | 607/40 |
| 5,716,385 | 2/1998 | Mittal et al. | 607/40 |
| 5,861,014 | 1/1999 | Familoni | 607/40 |

FOREIGN PATENT DOCUMENTS 0 684009A1  11/1995  European Pat. Off. .

OTHER PUBLICATIONS

DeVault, Kenneth R. et al., "Guidelines for the Diagnosis and Treatment of Gastroesophageal Reflux Disease," Arch Intern Med., vol. 155, Nov. 13, 1995, pp. 2165–2173.

Guyton, Arthur C., M.D., The Heart as a Pump, The Cardiac Cycle, Cardiac Contractility, and Stroke Volume Output, Textbook of Medical Physiology, 4th ed—illustrated, Chapter 13, pp. 148–161.

*Primary Examiner*—Jeffrey R. Jastrzab
*Attorney, Agent, or Firm*—Thomas F. Woods; Michael J. Jaro; Harold Patton

[57] ABSTRACT

There is provided a system and method for directly stimulating the LES of a patient in order to normally maintain it in a closed state, thereby preventing reflux and treating the symptoms of GERD. The stimulation is inhibited in response to patient swallowing, by monitoring esophageal motility and timing out an inhibition period following detection of motility representative of swallowing. The system utilizes an implanted stimulator which is programmed to deliver a train of stimulus pulses to one or more electrodes fixed around the gastro-esophageal junction and connected to the stimulator by one or more leads. The motility sensing is done by a sensor for sensing mechancial wave movement or electrical signals representative of high motility following swallowing. The motility sensor and stimulating electrodes are attached laproscopically, and are preferably carried by a common stent carrier which is sutured around the lower esophagus.

21 Claims, 4 Drawing Sheets

SYSTEM AND METHOD OF STIMULATION FOR TREATING GASTRO-ESOPHAGEAL REFLUX DISEASE

FIELD OF THE INVENTION

This invention lies in the field of implantable devices for treating gastro-esophagael reflux disease (GERD) and, more particularly, an implantable system for stimulating the lower esophageal sphincter (LES) so as to minimize reflux from the stomach into the esophagus.

BACKGROUND OF THE INVENTION

Gastro-esophageal reflux disease is a widespread affliction, which frequently elevates to be a clinical problem for the patient. It has been suggested that about ten percent of the U.S. population may have what is referred to as daily heartburn, and that more than one-third of the population has intermittent symptoms. See "Guidelines for the Diagnosis and Treatment of Gastro-Esophageal Reflux Disease," *Arch Intern Med.*, Fall, 155, Nov. 13, 1995. Most therapies for GERD, which has a number of different manifestations, have historically been directed at neutralization or suppression of gastric acid. Although the use of antacid for self-medication of symptoms of GERD is prodigious, unfortunately many patients with mild esophagitis nonetheless progress to a more severe form of the disease.

While it is commonly said that the underlying problem that produces GERD is abnormal acid secretion, the literature suggests that in fact it is largely an esophageal motility disorder. See "Guidelines for the Diagnosis and Treatment of Gastro-Esophageal Reflux Disease," DeVault and Castell, *Arch. Intern. Med.*, Vol. 155, Nov. 13, 1995, pp.2165–2173. By this it is meant that GERD is caused by abnormal motility which allows a breakdown of the anti-reflux barriers provided by the lower esophageal sphincter (LES) and esophageal-clearing peristalsis. The data point to decreased LES pressures in reflux patients. The more severe cases appear to be in patients having lower LES pressures with lower peristaltic amplitudes and abnormal peristalsis.

It is not clear whether the poor motility and low esophageal pressures of GERD patients precede esophageal mucosal reflux damage, or whether repeated reflux first results in a progressive decline in LES pressure. In any event, most patients with GERD who exhibit substantial esophageal injury also have abnormal LES pressures. One illustrative attempt to treat GERD with stimulation is shown in U.S. Pat. No. 5,716,385, Mittal et al. In that system, the skeletal muscles of the crural diaphragm are stimulated during relaxations of the diaphragm, causing contraction of the LES. However, this is a very indirect approach; the LES is not directly stimulated. Furthermore, the stimulation is applied only during sensed periods of transient relaxation.

By contrast, it is a premise of the system and method of this invention that therapy for GERD is best provided by substantially continuously increasing LES pressure. It is thus my concept to provide stimulation of the lower esophageal sphincter muscle to produce sustained and continuous contraction of the muscle so as to reduce acid reflux from the stomach. In other words, stimulation of the LES causes it to remain "tonal" or "excited," so that it is "closed" to a sufficient degree to reduce acid reflux from the stomach whenever there may be significant output of gastric acid. The induced constriction of the lower esophageal sphincter by application of stimulus pulses to excite the sphincter muscle will reduce, and indeed can stop ongoing acid damage within the esophagus. By thus correcting the GERD condition, the patient will be relieved from having to rely on costly drugs or surgical procedures, neither of which are reliably effective. Such an implantable system can be used to continuously correct the problem of lower LES pressure. The system can therefore provide a reduction in the number of medical problems, e.g., esophagitis (inflammation of the lower esophagus); bleeding from the lower esophagus due to ulcerations caused by acid reflux; reducing the risk of stricture formation of the lower esophagus from acid injury; and formation of scar tissue due to natural bodily attempts to heal the damaged area. Further, reduction of reflux injury can lower the incidence of cancer of the lower esophagus. In patients who are at increased risk due to Barrett's esophagus, reduction of acid reflux is likely also to reduce the risk of subsequent cancer.

SUMMARY OF THE INVENTION

In accordance with the above objective of stimulating the LES in order to alleviate a patient with GERD, there is provided an implantable stimulus system for substantially continuously stimulating the lower esophageal sphincter with a train of stimulus pulses so as to hold the sphincter in a "closed" state, thus stopping the reflux of gastric acid from the stomach to the esophagus. An implantable pulse generator device generates a train of stimulus pulses which are adapted in rate and energy level at the time of implantation and/or are programmed after implantation. The stimulus pulses are delivered through an array of electrodes which are affixed around the gastro-esophageal junction, by a laproscopic procedure, thereby normally holding the LES closed. A motility sensor is fixed on or in the esophagus above the gastro-esophageal junction, to provide an inhibiting signal to the stimulator whenever the patient swallows or exhibits esophageal peristalsis. The inhibiting signal stops generation of the pulse train for a duration which is timed to release the sphincter long enough to allow the food or liquid to pass from the esophagus through to the stomach.

DESCRIPTION OF THE PREFERRED EMBODIMENTS

The method and apparatus of this invention are intended for patients who have GERD, and for whom the procedure is indicated. Any patient who appears to be a candidate for the system of this invention first needs an esophageal manometry study, to determine whether the system would be helpful. If the study shows diffuse esophageal spasm, ie, the esophageal signals are not coordinated, this system will not work, and implant is not indicated. As described, the system of this invention requires accurate motility signals, and absent these the feedback for controlling the stimulation would not be available.

Figure 1:
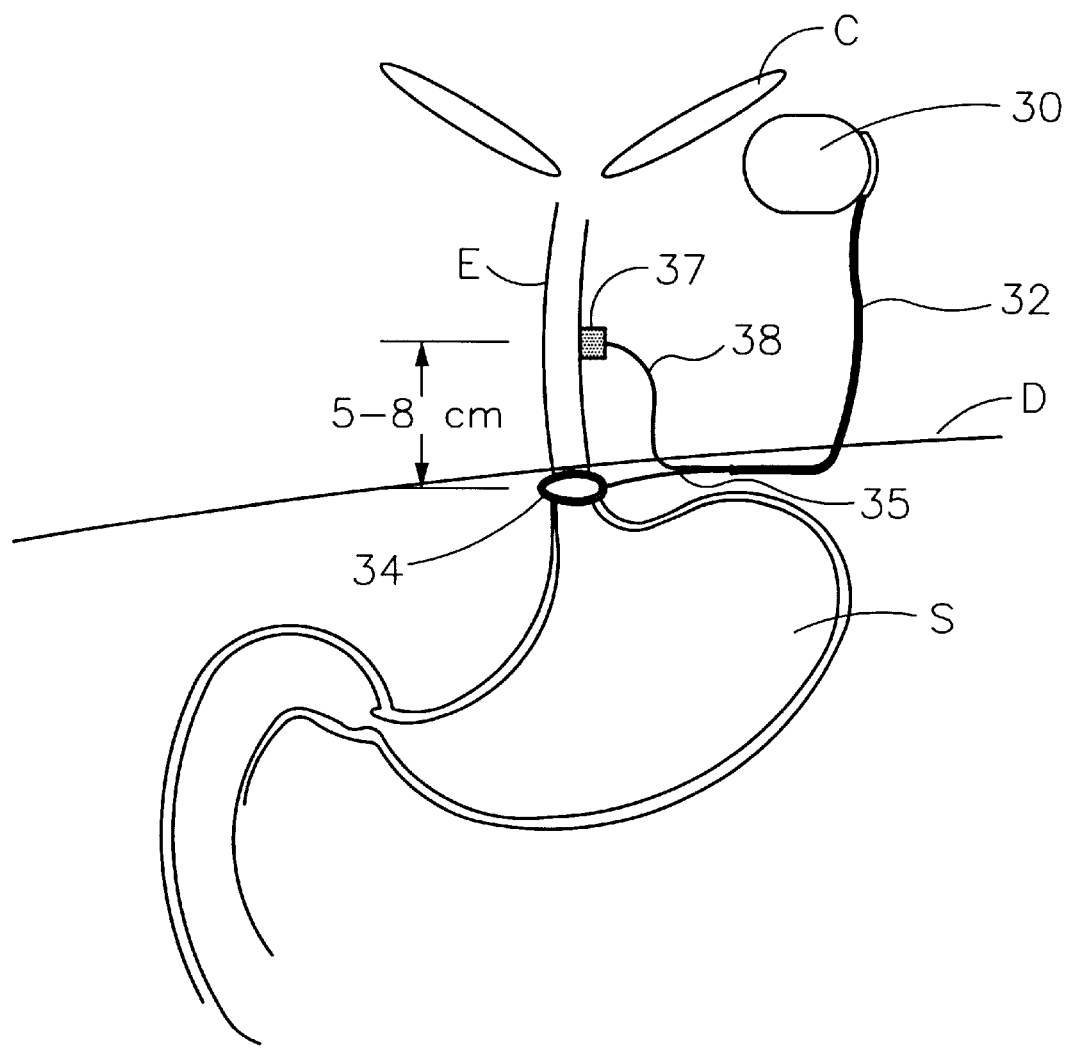
FIG. 1 is a diagrammatic view of a preferred embodiment of the system in accordance with this invention, showing the primary components of the system implanted in a patient.

Referring now to FIG. 1, there is shown a perspective diagram of a preferred embodiment of the system of this invention, as implanted in a patient. The components of the system are shown in place relative to the clavicle (designated "C") or collar bone area; the esophagus (E); the stomach (S); and the abdominal diaphragm (D). An implantable pulse generator device, or stimulator pack 30 is positioned suitably in the abdominal wall just below the clavicle area. Device 30, described in more detail in connection with FIG. 2, may be a commercially available device such as the Medtronic ITREL III pulse generator, or another stimulator designed to deliver a train of stimulus pulses for stimulating the LES. A lead 32, implanted subcutaneously, connects the device 30 electrically to electrodes 34 for stimulating the LES, and to a sensor or sensors 37 which sense esophageal motility. Electrodes 34 are suitably positioned on and/or around the LES at the gastro-esophageal junction, and may be carried by a collar or one or more metallic and/or fabric pieces that are sutured to the outer surface of the junction, thereby fixing the electrodes in place. A conductor 35, carried by lead 32 and electrically connected to the pulse generator output of device 30, delivers the stimulus pulses to the electrode or electrodes 34.

The stimulating pulses are generated at a suitable rate and with an efficient power for the desired stimulation of the LES, so as to hold it normally "tonal" or "closed," to thereby reduce acid reflux from the stomach. In practice, the pulse rate and parameters are chosen at time of implant, and adjusted for efficient and optimal excitation of the LES for the individual patient. As discussed below, the pulse parameters can subsequently be further adjusted by external programming.

Lead 32, which is tunneled through the diaphragm D, also carries one or more conductors 38, for connecting to sensor 37. Sensor 37 is affixed to the esophageal wall, suitably by suturing, and serves to sense normal episodes of motility, as occur when normal peristaltic waves are present during the act of swallowing. The signals from sensor 37 are transmitted back to the device 30, where the motility information is used to inhibit pulse delivery for a predetermined time period, e.g., 2–10 seconds, to relax the sphincter and enable the swallowed material to pass through the gastro-esophageal junction. While an objective is to maintain the LES in a normally constricted state so as to reduce reflux, it is obviously important to permit swallowing following food or drink intake, and sensor or sensors 37 provide the feedback control to enable this.

Figure 2:
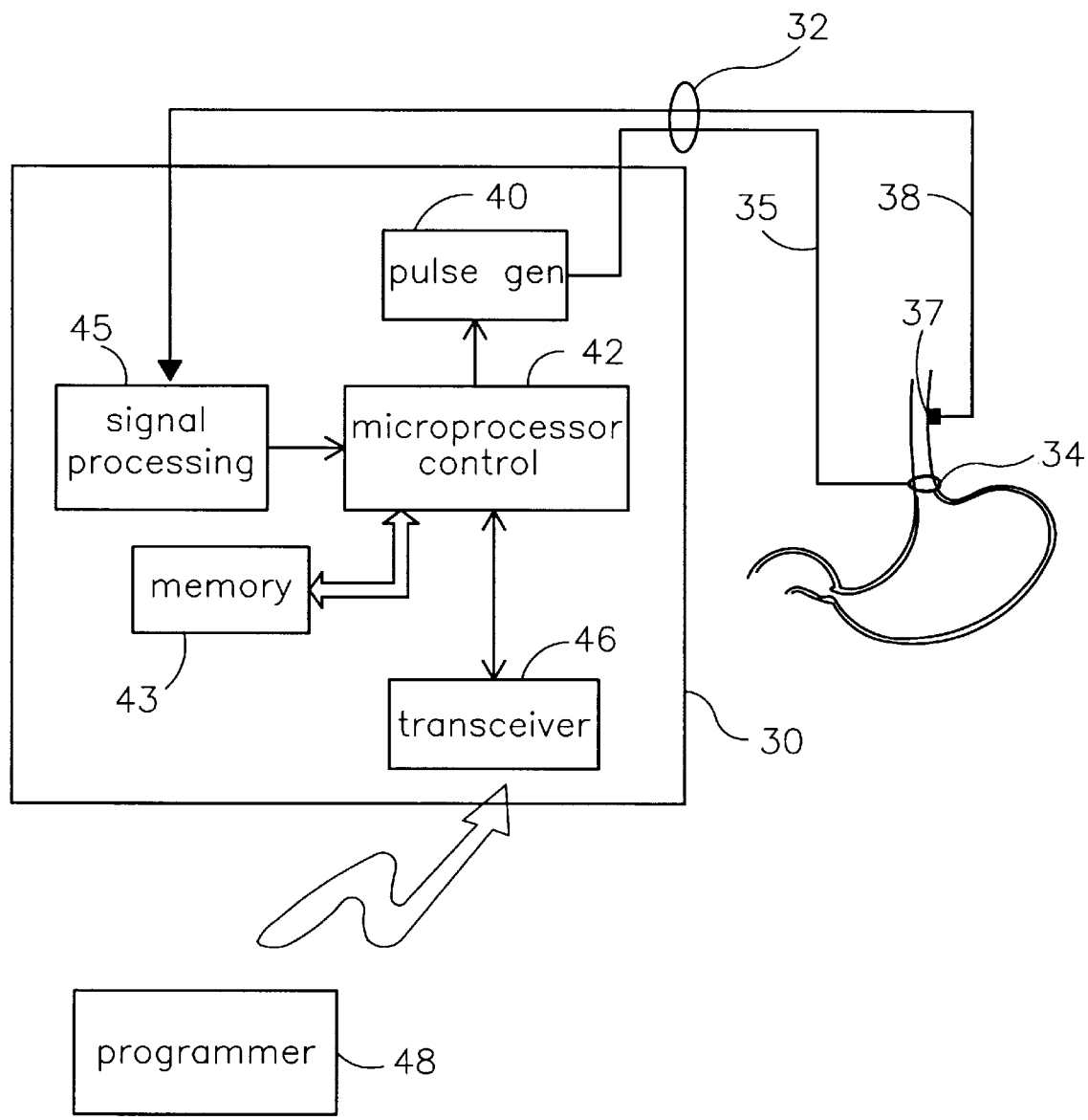
FIG. 2 is a block diagram illustrating the primary functional components of an implantable stimulus generator as used in this invention.

Referring now to FIG. 2, there is shown a block diagram of an implantable stimulus generator device for use with the system of this invention. The device may suitably be a Medtronic model ITREL III pulse generator, or a modification thereof. The device is battery powered, in a well known manner. As illustrated, the device 30 has a pulse generator circuit 40, for generating a train of stimulus pulses. The rate of pulse generation is variable, and is controlled by control block 42. Block 42 preferably contains a microprocessor and associated built-in memory, as well as requisite timing circuits. The microprocessor control inter-connects with memory 43, which can store a record of data obtained by the device, provide RAM routines, etc. A transceiver 46 provides telemetric communication with an external programmer 48, in a fashion well known in the pacemaker art, for receiving new instructions, data for programming the pulse parameters, etc. Thus, the rate, amplitude, duty cycle, etc. of the pulse train provided by generator 40 can by programmed externally. Additionally, the programmer can be used by the patient to stop or turn off operation of the stimulator, which might be useful in certain circumstances, such as sickness.

The pulses generated by circuit 40 are connected onto conductor 35, which connects to the device 30 as part of lead 32. Conductor 35 connects the stimulus pulses to the electrodes represented in FIG. 2 by ring 34. Motility sensor 37 is connected by conductor 38 to signal processing circuitry 45 within device 30. Sensor 37 is suitably a piezo-electric type sensor for detecting mechanical movements or acceleration; a conventional electrode for detecting electrical signals representative of the motility; an impedance sensor; or any other available sensor for detecting esophageal movement. Sensor 37 can suitably be placed on a soft helical net which is wrapped around the esophagus, attached with small stay sutures. Circuitry 45 may include conventional amplifier and filtering circuitry; it may also include digitizing circuitry for providing digital signals for digital signal processing. Block 45 includes circuitry for recognizing when a motility signal from sensor(s) 37 indicates normal motility waves representative of swallowing, or a peristaltic episode of a magnitude to stop stimulation of the LES. This is done, e.g., by detecting the occurrence of waves having an amplitude above a predetermined threshold and recurring for a predetermined number of cycles. The circuit may also compare sensed signals to a stored pattern, for motility detection. In response to such a recognized episode, circuitry 45 produces an inhibit signal, which is received by control block 42; block 42 responds by inhibiting operation of generator 40 for a predetermined period of time, e.g., 2–10 seconds. Circuitry 45 may produce consecutive inhibit signals, in which case generator 42 could be inhibited continuously as long as the episodes continued substantially uninterrupted. Of course, it is to be understood that the logic of inhibiting the pulse generator can be carried out by any desired combination of analog and software processing in circuits 40 and 45.

Figure 3A:
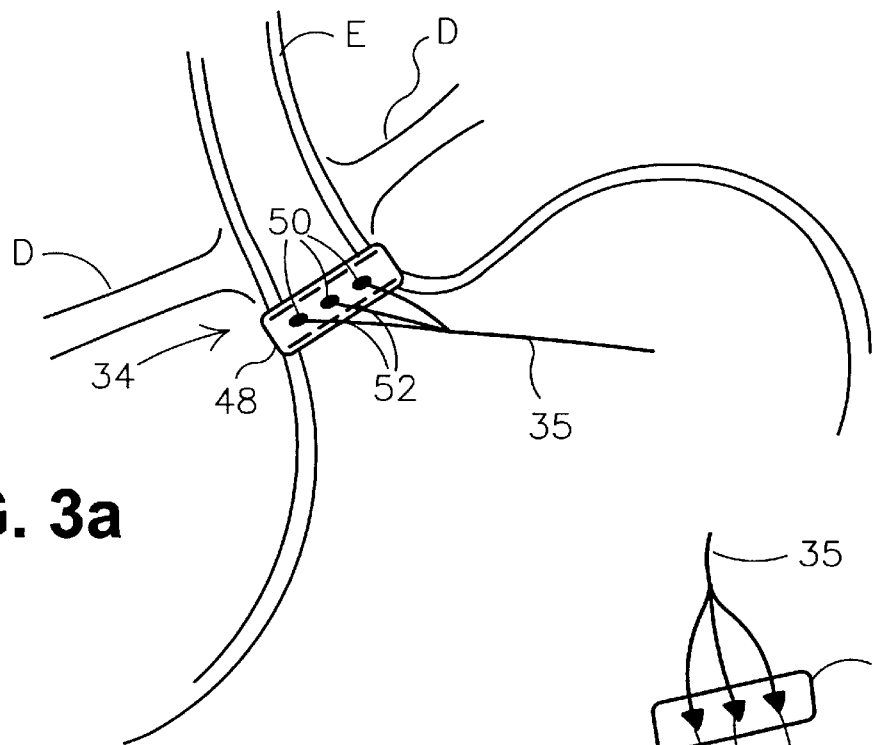
FIG. 3a is a perspective view illustrating an array of electrodes sutured in place around in gastro-esophageal junction of a patient, for delivering stimulus pulses to the lower esophageal sphincter.
Figure 3B:
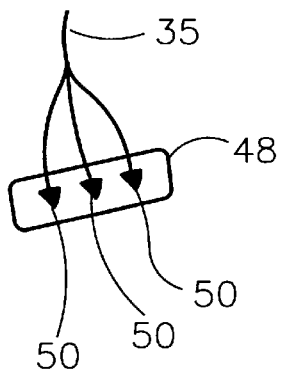
FIG. 3b is a view of the electrode array as seen from the inside surface of a collar piece, illustrating the electrodes which are fixed to pierce into the outer muscle in the region of the LES.

Referring now to FIG. 3a, there is shown a perspective view of an element 48 which carries an array 34 of electrodes affixed to the outside surface of the gastro-esophageal junction for stimulation of the LES, where the electrodes are shown directed away from the viewer and toward the junction; FIG. 3b shows the same array, looking at the carrier surface that is attached inward to the junction. A carrier element 48 is shown sutured onto the outside of the junction, as indicated by sutures 52. The carrier may be any suitable biocompatible material, such as a woven fabric. The carrier is flexible, and can stretch in response to enlargement of the esophagus, yet retract to its original size. Individual sensors 50 are attached to the carrier, having pointed electrode elements directed so that the electrode tips penetrate into the junction muscle when the carrier is sutured into place on the junction. The electrode elements may be made of conventional electrode material, e.g., platinum-iridium. Since the esophagus does not have a serosal layer, the electrodes need only extend about a mm or so into the muscle. One or more carriers 48 may be laproscopically sutured on the junction, each one carrying one or more electrodes.

Figure 4:
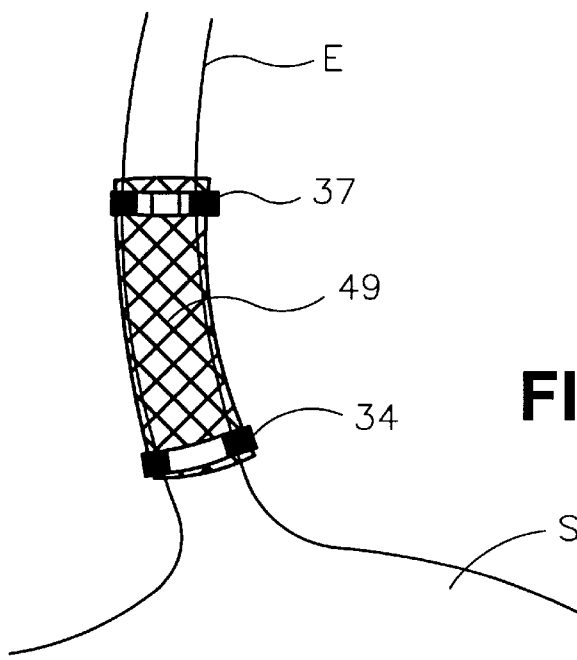
FIG. 4 is a schematic drawing showing placement of a stent around the lower esophagus, the stent carrying a motility sensor at its proximal end and the electrode array at its distal end.

Referring to FIG. 4, there is shown a schematic diagram of a preferred embodiment constituting a flexible stent-like cylinder 49 which carries the motility sensor 37 at the proximal end, and the stimulation array 34 at the distal end. The stent element is woven of metallic or other biocompatible fabric material; it is normally in a tight (but not constricting) engagement with the esophagus, but is expandable to accomodate enlargement of the esophagus. It is placed laproscopically, with a few stay sutures.

Figure 5:
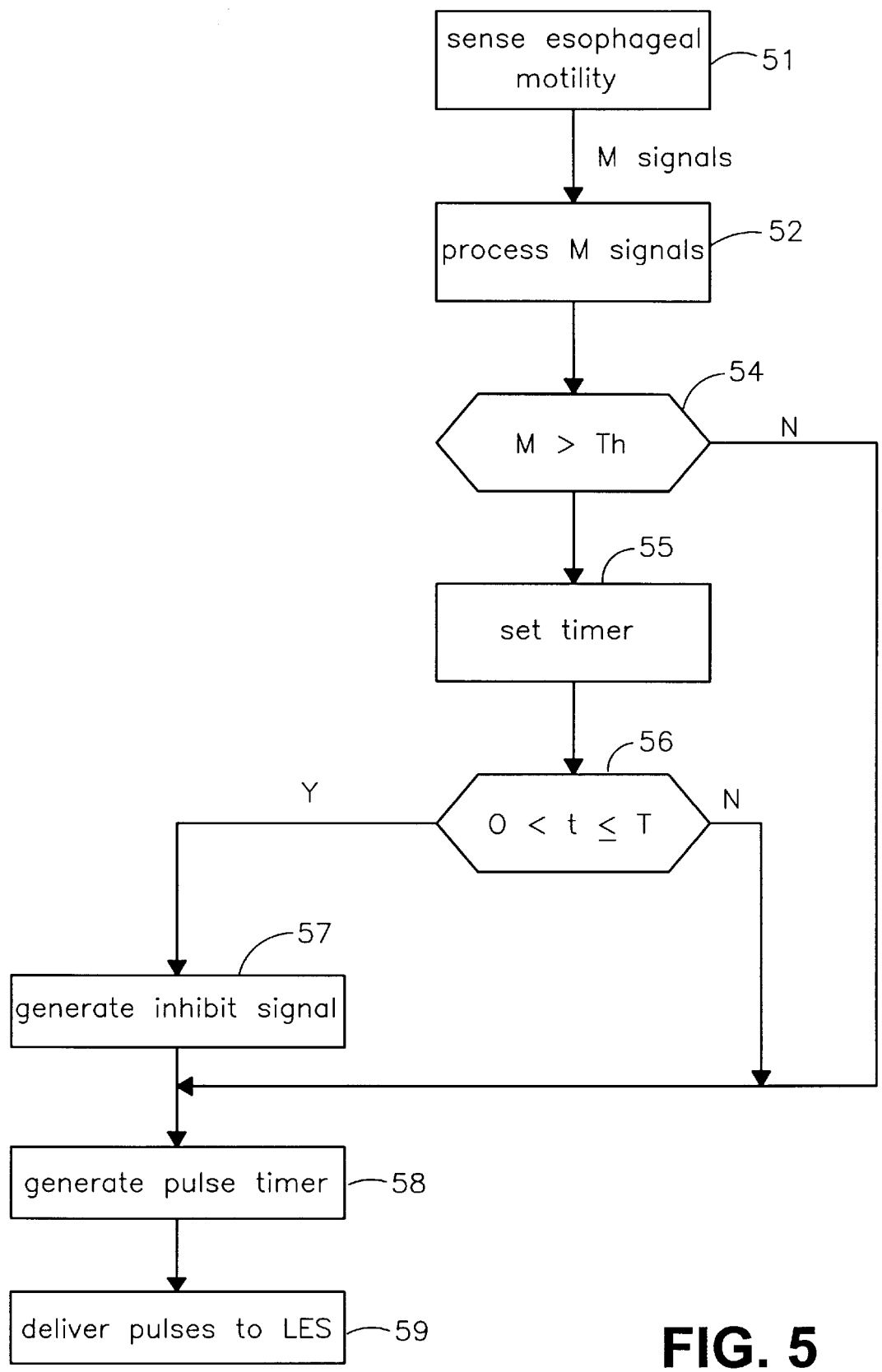
FIG. 5 is a flow diagram illustrating the actions taken in delivering stimulus pulses to the LES electrodes, and in controlling the generation of the stimulus pulses.

Referring now to FIG. 5, there is shown a flow diagram representing the pulse generator control as utilized in the system and method of this invention. As indicated at 51, esophageal motility is continually sensed. Signals, represented as M signals, are generated by transducer 37 and processed at 52. The processed M signals are analyzed at 54 to determine whether and when they reflect swallowing or any normal esophageal action requiring an open path to the stomach. Thus, at 54 the amplitude of M can be compared to a predetermined threshold; alternately the time or frequency characteristics of the signals can be compared to a stored profile of a true peristaltic movement. When a true peristaltic episode is detected, a timer is set, as indicated at 55, to time out an inhibit period T of a few seconds, e.g., 2–10 seconds; the value of T can be programmed to accomodate each patient. Note that if M signals are received continuously at 54, the timer will be reset continuously until the episode terminates. At 56, it is determined whether the timer is running, i.e., an episode period is being timed out. If yes, at 57 the system inhibits the generator from its normal condition of generating pulses and delivering them to the LES (58,59); if no, the generator is not inhibited, ie, normal stimulation of the LES is maintained.

There has been disclosed a system and method for treating GERD, which directly attacks the problem by normally holding the LES in a closed state. The system utilizes stimulation of the LES to activate the muscle to contract, and utilizes esophageal motility feedback inhibit stimulation and to release the LES when required for swallowing. The system thus provides a simple but reliably effective method of treatment.

What is claimed is:

1. A system for treating gastro-esophageal reflux by stimulation of the lower esophageal sphincter of a patient, comprising:

a stimulator for generating stimulus pulses;

delivery means for delivering said stimulus pulses to said sphincter;

sensing means for sensing episodes of esophageal motility; and inhibiting means for inhibiting said stimulator following a sensed episode of esophageal motility.

2. The system as described in claim 1, wherein said stimulator comprises a pulse generator for normally generating a continuous train of said stimulus pulses.

3. The system as described in claim 2, wherein said delivery means comprises electrode means for positioning an array of electrodes in the area of the patient's gastro-esophageal junction.

4. The system as described in claim 2, wherein said delivery means comprises electrode means for fixing at least one electrode to the patient's gastro-esophageal junction, and connecting means for connecting said pulses to said at least one electrode.

5. The system as described in claim 4, wherein said electrode means comprises a plurality of electrodes, and fixing means for affixing said electrodes around said gastro-esophageal junction so that said stimulus pulses excite said sphincter to a closed condition.

6. The system as described in claim 5, wherein said electrode means comprises an array of electrodes suitable for fixation substantially circumferentially around said gastro-esophageal junction.

7. The system as described in claim 6, wherein said sensing means comprises a motility sensor suitable for attachment to the patient's esophagus, and comprising stent means for carrying said motility sensor and said electrode means.

8. The system as described in claim 1, wherein said sensing means comprises accelerometer means for generating signals representative of peristaltic motion, and said inhibiting means comprises signal processing means for processing said representative signals to generate inhibition signals indicative of the timing of said episodes.

9. The system as described in claim 8, wherein said inhibiting means comprises circuit means for inhibiting generation of stimulus pulses by said generator upon generation of a said inhibition signal.

10. The system as described in claim 1, wherein said inhibition means comprises timing means for inhibiting said generator for a predetermined time period following a said sensed episode.

11. The system as described in claim 10, wherein said timing means times out an inhibition period having a duration in the range of 2 to 10 seconds.

12. The system as described in claim 1, wherein said delivery means comprises one or more electrodes suitable for being positioned laterally on the lower esophageal junction, and said sensing means includes a motility sensor suitable for positioning at least about 5 cm above said one or more electrodes.

13. The system as described in claim 1, wherein said sensing means comprises at least one sensor suitable for positioning on the patient's esophagus and about 5–8 cm above the patient's lower esophageal junction.

14. The system as described in claim 1, wherein said sensing means comprises at least one sensing element suitable for suturing to the patient's esophagus above said sphincter.

15. A system for treating GERD, comprising:

stimulating means for normally continuously and directly stimulating a patient's LES so as to maintain it in a substantially closed state; and inhibiting means for inhibiting said normal stimulating as a function of motility in the patient's esophagus.

16. The system as described in claim 15, wherein said stimulating means comprises electrode means connected at about the patient's gastro-esophageal junction, and motility sensing means positioned on the patient's esophagus above said junction.

17. The system as described in claim 16, comprising carrier means for carrying said electrode means and said motility sensing means.

18. The system as described in claim 16, wherein said inhibiting means comprises signal processing means for processing motility signals from said motility sensing means, and timing means for inhibiting stimulation of the patient's LES in response to detection of motiltiy signals representative of patient swallowing.

19. A method of treating GERD in a patient, comprising:

directly stimulating the LES of a patient, said stimulating being normally continuous so as to maintain said LES in a substantially closed state; and sensing esophageal motility in said patient, and inhibiting said stimulating in response to sensed motility which is representative of swallowing.

20. The method as described in claim 19, comprising inhibiting stimulating for a period in the range of about 2–10 seconds following swallowing by said patient.

21. A system for treating gastro-esophageal reflux by stimulation of the lower esophageal sphincter of a patient, comprising:

a stimulator for generating stimulus pulses;

delivery means for delivering said stimulus pulses to said sphincter;

sensing means for sensing episodes of esophageal motility; and inhibiting means for inhibiting said stimulator following a sensed episode of motility, wherein said delivery means for delivering said stimulus pulses to said sphincter comprises one of a collar, one or more metallic pieces, and one or more fabric pieces suitable for suturing to said lower esophageal sphincter.

* * * * *